United States Patent [19]

Tremaine

[11] Patent Number: 5,013,071
[45] Date of Patent: May 7, 1991

[54] FINGERPRINTING SYSTEM

[76] Inventor: David K. Tremaine, P.O. Box 4556, San Diego, Calif. 92104

[21] Appl. No.: 423,389

[22] Filed: Oct. 19, 1989

[51] Int. Cl.⁵ .................................................. B42D 15/00
[52] U.S. Cl. ........................................ 283/69; 283/68; 283/78
[58] Field of Search .............................. 283/68, 78, 69

[56] References Cited

U.S. PATENT DOCUMENTS

| | | | |
|---|---|---|---|
| 1,607,946 | 11/1926 | Crosskey | 283/78 |
| 2,606,744 | 7/1935 | Pierce | 283/78 |
| 2,912,259 | 11/1959 | Young | 283/78 |
| 3,447,818 | 6/1969 | Pizzol | 283/68 |
| 3,664,910 | 5/1972 | Hollie | 283/78 |
| 4,669,753 | 6/1987 | Land et al. | 283/70 |
| 4,706,600 | 11/1987 | Mason, Jr. et al. | 283/78 |
| 4,943,089 | 7/1990 | Reardon | 283/68 |

Primary Examiner—Douglas D. Watts
Assistant Examiner—Hwei-Siu Payer
Attorney, Agent, or Firm—Charles C. Logan, II

[57] ABSTRACT

The improved fingerprinting system utilizes a conventional fingerprint card having a fingerprint portion on its top surface. A multi-layered sheet having dimensions approximating that of the fingerprint portion has a layer of adhesive material sandwiched between a front liner sheet and a rear liner sheet. The rear liner sheet is removed thereby allowing the layer of adhesive material to be pressed into contact with the fingerprint portion of the fingerprint card. The front liner sheet is transversely scored to form a plurality of strips. One strip at a time is removed to allow fingerprint impressions to be pressed into the respective frames of the particular row of the fingerprint portion. After all of the rows have received their fingerprint impressions, a transparent sheet of plastic material is applied to the top surface of the layer of adhesive material.

2 Claims, 1 Drawing Sheet

FINGERPRINTING SYSTEM

BACKGROUND OF THE INVENTION

The invention relates to fingerprinting and more specifically to an improved fingerprinting system.

Presently police departments and other government agencies utilize the same or very similar fingerprint cards. These cards have a heading portion and a fingerprint portion. The fingerprint portion usually consists of three transversely extending rows. These rows are broken up into frames for receiving the individual fingerprints of the respective fingers of the left and right hands of an individual. The bottom row is divided into frames that receive imprints of the fingers taken simultaneously together.

The process for fingerprinting an individual requires that the individual have ink applied to their fingertips and then the finger is pressed downwardly into its identified frame with a rolling motion to give a complete imprint thereof. The ink utilized for making the fingerprints normally takes at least a half hour to dry. As a result, the fingerprints on the cards can be smudged very easily if proper care is not taken to prevent from being covered before they are completely dry. Sometimes this means that a new set of fingerprints must be taken and this results in an unnecessary waste of the police personnel's time.

It is an object of the invention to provide a novel improved fingerprinting system that will produce fingerprints having more clarity than the presently existing system.

It is also an object of the invention to provide a novel improved fingerprinting system that is smear proof.

It is another object of the invention to provide an improved fingerprinting system that has a drying time of near zero.

It is an additional object of the invention to provide a novel improved fingerprinting system that is tamperproof.

SUMMARY OF THE INVENTION

Applicant's novel improved fingerprinting system utilizes the basic conventional fingerprint card that has been used for as long as one can remember. These fingerprint cards have a heading portion and a fingerprint portion. The fingerprint portion consists of three transversely extending rows that are divided into individual frames for receiving a fingerprint impression for a specific finger.

The improved fingerprinting system utilizes two additional sheets of material. The first sheet is a sandwich-like structure having a layer of adhesive between a front liner sheet and a rear liner. This first sheet has dimensions approximating that of the fingerprint portion of the fingerprint card. The first step in utilizing the first sheet is to remove the rear liner sheet thus exposing the layer of adhesive. This adhesive layer is then positioned over the fingerprint portion and pressed into contact therewith. At this time the fingerprint card is inserted into a conventional fingerprint card holder. Next a transversely extending strip of the front liner sheet is removed from the layer of adhesive material and the person who is being fingerprinted has their right fingers inked and imprinted in the respective frames of row one. When this step is completed, the transversely extending strip is then replaced onto the adhesive layer of row one. The fingerprint card is adjusted in the fingerprint card holder so that the second row is in position. The transverse strip of that row is then removed from the adhesive layer and the individual fingers of the left hand are imprinted thereon. As done previously, the transverse strip is replaced on the top surface of the adhesive layer of row two. The fingerprint card is adjusted in the holder so that row three is now in position. The transverse strip of the front liner sheet is then removed and the fingerprints that are taken simultaneously with the respective hands are imprinted on the top surface of the adhesive layer of material. The fingerprint card is then removed from the holder and the transverse strips of the front liner sheet that covers rows one and two are removed.

The second sheet that is utilized with applicant's novel improved fingerprinting system is now used. It consists of a transparent sheet of plastic material having a layer of transparent adhesive material on its rear surface and a rear liner sheet covers the adhesive material. This rear liner sheet is removed and the sheet of transparent plastic material is then placed over the fingerprint portion and pressed into contact therewith.

The adhesive layer into which the persons finger is pressed to form a fingerprint impression provides more clarity for the print itself. Also since the sheet of transparent plastic material is covering the recently made fingerprints, there is a dry-time of near zero and the fingerprints become near smear proof. Additionally, the completed fingerprint card is tamper proof since any attempts to remove the transparent plastic sheet of material will destroy the fingerprint impression thereunder by tearing the paper of the fingerprint card.

DESCRIPTION OF THE PREFERRED EMBODIMENT

Figure 1:
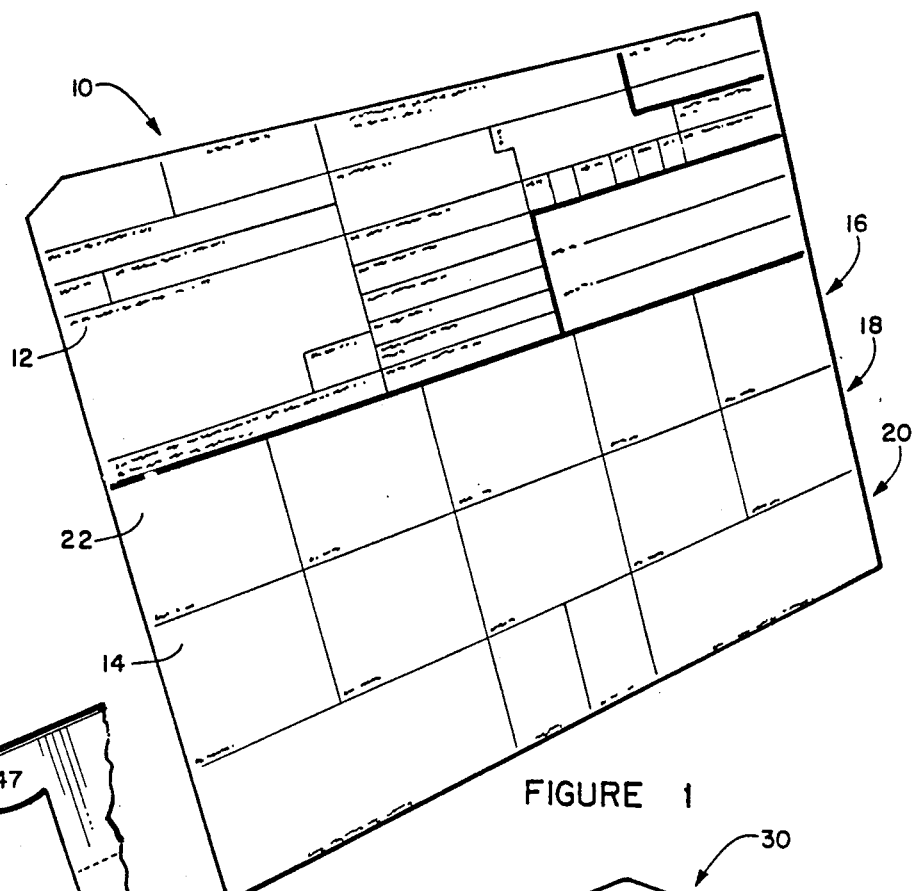
FIG. 1 is a top plan view of a conventional fingerprint card.
Figure 3:
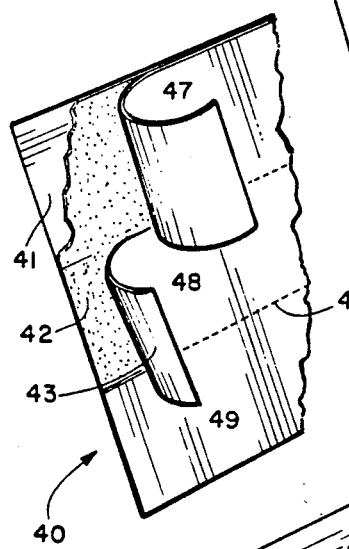
FIG. 3 is a front exploded perspective view of a portion of sheet number 40.

Applicant's novel improved fingerprinting system will now be described by referring to FIGS. 1-4 of the drawing.

A standard conventional fingerprint card 10 is illustrated in FIG. 1. It has a heading portion 12 and a fingerprint portion 14. Fingerprint portion 14 has contiguous transversely extending rows 16, 18 and 20. These respective rows have individual frames 22 for each of the individual fingerprints.

Figure 2:
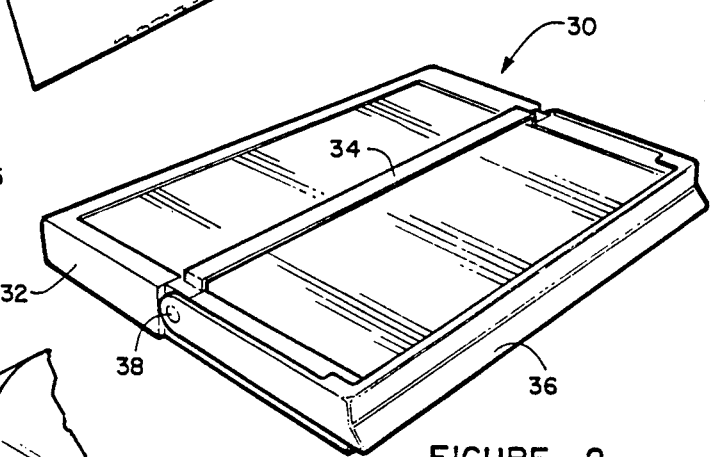
FIG. 2 is a front perspective view of a conventional fingerprint card holder.
Figure 4:
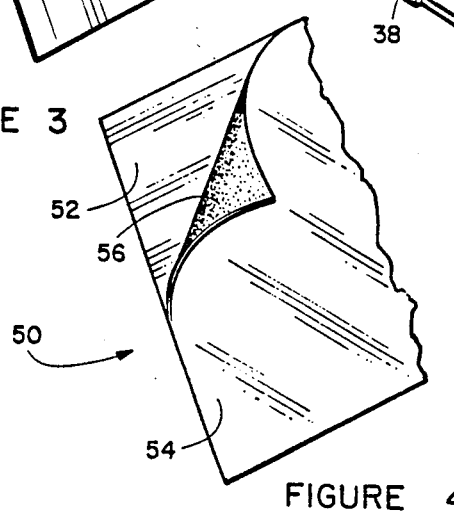
FIG. 4 is a front perspective view of sheet number 50.

Fingerprint card holder 30 is illustrated in FIG. 2. It has a base 32 and a transversely extending fingerprint card holddown member 34. A holddown arm 36 is pivoted about pins 38.

A primary sheet is generally designated numeral 40. It has a rear liner sheet 41, a layer of transparent adhesive material 42, and a front liner sheet 43. Score lines 45 extend transversely along front liner sheet 43 to form strips 47, 48 and 49.

A secondary sheet is generally designated numeral 50. It has a rear cover liner sheet 52 and a transparent plastic sheet 54. The rear surface of transparent sheet 54 has a transparent layer of adhesive 56.

What is claimed is:

1. An improved method of taking fingerprints comprising the following steps:
   (a) providing a conventional fingerprint card having a top surface with a heading portion and a fingerprint portion printed thereon and placing the fingerprint card on a support surface with its top surface facing upwardly;
   (b) providing a predetermined sheet having a bottom liner and a top liner and having a layer of adhesive material therebetween, removing the bottom liner to expose the layer of adhesive material and pressing it onto the fingerprint portion of the fingerprint card which causes the layer of adhesive material to adhere to the top surface of the fingerprint portion;
   (c) removing the top liner from the layer of adhesive that is now adhered to the top surface of the fingerprint portion of the fingerprint card;
   (d) applying fingerprint impressions of an individual to the fingerprint portion of the fingerprint card;
   (e) providing a transparent sheet of plastic material having a bottom surface with a layer of adhesive thereon that is covered with a cover liner sheet, removing the cover liner sheet and applying the bottom surface of the plastic material to the top surface of said layer of adhesive material on the fingerprint portion of said fingerprint card.

2. An improved method of taking fingerprints comprising the following steps:
   (a) providing a conventional fingerprint card having a top surface with a heading portion and a fingerprint portion printed thereon, the fingerprint portion has a first, second and third row of frames, placing the fingerprint card on a support surface with its top surface facing upwardly;
   (b) providing a predetermined sheet having a bottom liner and a top liner and having a layer of adhesive material therebetween, removing the bottom liner to expose the layer of adhesive material and pressing it onto the fingerprint portion of the fingerprint card which causes the layer of adhesive material to adhere to the top surface of the fingerprint portion;
   (c) removing a transversely extending strip of said top liner;
   (d) applying fingerprint impressions of an individual to the first row of frames of the fingerprint portion;
   (e) replacing the previously removed transversely extending strip of said top liner in its original position on the layer of adhesive material;
   (f) repeating steps (c), (d) and (e) for the remaining transversely extending strips of said top liner that cover the respective second and third row frames of said fingerprint portion;
   (g) removing all the transversely extending strips of said top liner from said fingerprint portion;
   (h) providing a transparent sheet of plastic material having a bottom surface with a layer of adhesive thereon that is covered with a cover liner sheet, removing the cover liner sheet and applying the bottom surface of the plastic material to the top surface of said layer of adhesive material on the fingerprint portion of said fingerprint card.

* * * * *